US008110582B2

(12) United States Patent
Egging et al.

(10) Patent No.: US 8,110,582 B2
(45) Date of Patent: Feb. 7, 2012

(54) PROPHYLACTIC TREATMENT OF UV-INDUCED EPIDERMAL NEOPLASIA

(75) Inventors: Elaine A. Egging, Woodbury, MN (US); David M. Hammerbeck, Houlton, WI (US); James H. Lee, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 1003 days.

(21) Appl. No.: 10/793,293

(22) Filed: Mar. 4, 2004

(65) Prior Publication Data
US 2004/0175336 A1 Sep. 9, 2004

Related U.S. Application Data

(60) Provisional application No. 60/451,699, filed on Mar. 4, 2003.

(51) Int. Cl.
*A61K 31/44* (2006.01)
*A61K 31/415* (2006.01)
(52) U.S. Cl. ......... 514/279; 514/385; 514/396; 514/397
(58) Field of Classification Search .................... 424/59; 514/279, 385, 396, 397
See application file for complete search history.

(56) References Cited

U.S. PATENT DOCUMENTS

| 4,689,338 | A |   | 8/1987 | Gerster |
|---|---|---|---|---|
| 4,698,348 | A |   | 10/1987 | Gerster |
| 4,847,071 | A | * | 7/1989 | Bissett et al. .................... 424/59 |
| 4,929,624 | A |   | 5/1990 | Gerster et al. |
| 4,988,815 | A |   | 1/1991 | Andre et al. |
| 5,037,986 | A |   | 8/1991 | Gerster |
| 5,175,296 | A |   | 12/1992 | Gerster |
| 5,238,944 | A |   | 8/1993 | Wick et al. |
| 5,266,575 | A |   | 11/1993 | Gerster et al. |
| 5,268,376 | A |   | 12/1993 | Gerster |
| 5,346,905 | A |   | 9/1994 | Gerster |
| 5,352,784 | A |   | 10/1994 | Nikolaides et al. |
| 5,367,076 | A |   | 11/1994 | Gerster |
| 5,376,501 | A |   | 12/1994 | Mariën et al. |
| 5,389,640 | A |   | 2/1995 | Gerster et al. |
| 5,395,937 | A |   | 3/1995 | Nikolaides et al. |
| 5,446,153 | A |   | 8/1995 | Lindstrom et al. |
| 5,482,936 | A |   | 1/1996 | Lindstrom |
| 5,494,916 | A |   | 2/1996 | Lindstrom et al. |
| 5,525,612 | A |   | 6/1996 | Gerster |
| 5,605,899 | A |   | 2/1997 | Gerster et al. |
| 5,693,811 | A |   | 12/1997 | Lindstrom |
| 5,741,908 | A |   | 4/1998 | Gerster et al. |
| 5,756,747 | A |   | 5/1998 | Gerster |
| 5,939,090 | A |   | 8/1999 | Beaurline et al. |
| 6,028,076 | A |   | 2/2000 | Hirota et al. |
| 6,039,969 | A |   | 3/2000 | Tomai et al. |
| 6,069,149 | A |   | 5/2000 | Nanba et al. |
| 6,083,505 | A |   | 7/2000 | Miller et al. |
| 6,110,929 | A |   | 8/2000 | Gerster et al. |
| 6,113,918 | A |   | 9/2000 | Johnson et al. |
| 6,194,388 | B1 |   | 2/2001 | Krieg et al. |
| 6,194,425 | B1 |   | 2/2001 | Gerster et al. |
| 6,200,592 | B1 |   | 3/2001 | Tomai et al. |
| 6,207,646 | B1 |   | 3/2001 | Krieg et al. |
| 6,239,116 | B1 |   | 5/2001 | Krieg et al. |
| 6,245,776 | B1 |   | 6/2001 | Skwierczynski et al. |
| 6,303,347 | B1 |   | 10/2001 | Johnson et al. |
| 6,323,200 | B1 |   | 11/2001 | Gerster et al. |
| 6,329,381 | B1 |   | 12/2001 | Kurimoto et al. |
| 6,331,539 | B1 |   | 12/2001 | Crooks et al. |
| 6,339,068 | B1 |   | 1/2002 | Krieg et al. |
| 6,376,501 | B1 |   | 4/2002 | Isobe et al. |
| 6,376,669 | B1 |   | 4/2002 | Rice et al. |
| 6,387,938 | B1 |   | 5/2002 | Mizuguchi et al. |
| 6,406,705 | B1 |   | 6/2002 | Davis et al. |
| 6,426,334 | B1 |   | 7/2002 | Agrawal et al. |
| 6,440,992 | B1 |   | 8/2002 | Gerster et al. |
| 6,451,810 | B1 |   | 9/2002 | Coleman et al. |
| 6,476,000 | B1 |   | 11/2002 | Agrawal |
| 6,514,985 | B1 |   | 2/2003 | Gerster et al. |
| 6,518,265 | B1 |   | 2/2003 | Kato et al. |
| 6,518,280 | B2 |   | 2/2003 | Gerster et al. |
| 6,525,028 | B1 |   | 2/2003 | Johnson et al. |
| 6,525,064 | B1 |   | 2/2003 | Dellaria et al. |
| 6,541,485 | B1 |   | 4/2003 | Crooks et al. |
| 6,545,016 | B1 |   | 4/2003 | Dellaria et al. |
| 6,545,017 | B1 | * | 4/2003 | Dellaria et al. ................ 514/303 |
| 6,558,951 | B1 |   | 5/2003 | Tomai et al. |
| 6,573,273 | B1 |   | 6/2003 | Crooks et al. |
| 6,649,172 | B2 |   | 11/2003 | Johnson |
| 6,656,938 | B2 |   | 12/2003 | Crooks et al. |
| 6,660,735 | B2 |   | 12/2003 | Crooks et al. |
| 6,660,747 | B2 |   | 12/2003 | Crooks et al. |
| 6,664,260 | B2 |   | 12/2003 | Charles et al. |
| 6,664,264 | B2 |   | 12/2003 | Dellaria et al. |
| 6,664,265 | B2 |   | 12/2003 | Crooks et al. |
| 6,667,312 | B2 |   | 12/2003 | Bonk et al. |
| 6,670,372 | B2 |   | 12/2003 | Charles et al. |
| 6,677,347 | B2 |   | 1/2004 | Crooks et al. |
| 6,677,348 | B2 |   | 1/2004 | Heppner et al. |
| 6,677,349 | B1 |   | 1/2004 | Griesgraber |
| 6,683,088 | B2 |   | 1/2004 | Crooks et al. |

(Continued)

FOREIGN PATENT DOCUMENTS

EP 0 394 026 10/1990

(Continued)

OTHER PUBLICATIONS

Testerman, et al., "Cytokine Induction by the Immunomodulators Imiquimod and S-27609", *Journal of Leukocyte Biology*, vol. 58, pp. 365-372, Sep. 1995.

(Continued)

*Primary Examiner* — James H. Alstrum-Acevedo

(57) ABSTRACT

The present invention provides a method of protecting a subject against UV-induced epidermal neoplasia. Generally, the method includes administering to a subject an IRM compound in an amount effective to provide protection against UV-induced epidermal neoplasia. The present invention also provides compositions that include an IRM compound in an amount effective for providing protection against UV-induced epidermal neoplasia.

10 Claims, No Drawings

U.S. PATENT DOCUMENTS

| | | |
|---|---|---|
| 2002/0016332 A1 | 2/2002 | Slade |
| 2002/0055517 A1 | 5/2002 | Smith |
| 2002/0058674 A1 | 5/2002 | Hedenstrom et al. |
| 2002/0110840 A1 | 8/2002 | Tomai et al. |
| 2003/0022302 A1 | 1/2003 | Lewis et al. |
| 2003/0133913 A1 | 7/2003 | Tomai et al. |
| 2003/0139364 A1 | 7/2003 | Krieg et al. |
| 2003/0144283 A1 | 7/2003 | Coleman et al. |
| 2003/0199461 A1 | 10/2003 | Averett et al. |
| 2003/0199538 A1* | 10/2003 | Skwierczynski et al. ..... 514/291 |
| 2004/0010007 A1 | 1/2004 | Dellaria et al. |
| 2004/0014779 A1 | 1/2004 | Gorden et al. |
| 2004/0023870 A1 | 2/2004 | Dedera et al. |

FOREIGN PATENT DOCUMENTS

| | | |
|---|---|---|
| EP | 1 104 764 A1 | 6/2001 |
| JP | 9-208584 | 8/1997 |
| JP | 10-510803 | 10/1998 |
| JP | 11-80156 | 3/1999 |
| JP | 11-222432 | 8/1999 |
| JP | 2000-247884 | 9/2000 |
| WO | WO 00/47719 A2 | 8/2000 |
| WO | WO 00/75304 A1 | 12/2000 |
| WO | WO 00/76505 A1 | 12/2000 |
| WO | WO 00/76518 A1 | 12/2000 |
| WO | WO 01/74343 A2 | 10/2001 |
| WO | WO 02/36592 A1 | 5/2002 |
| WO | WO 02/46188 A2 | 6/2002 |
| WO | WO 02/46189 A2 | 6/2002 |
| WO | WO 02/46190 A2 | 6/2002 |
| WO | WO 02/46191 A2 | 6/2002 |
| WO | WO 02/46192 A2 | 6/2002 |
| WO | WO 02/46193 A2 | 6/2002 |
| WO | WO 02/46194 A2 | 6/2002 |
| WO | WO 02/46749 A2 | 6/2002 |
| WO | WO 02/085905 A1 | 10/2002 |
| WO | WO 02/102377 A1 | 12/2002 |
| WO | WO 03/020889 A2 | 3/2003 |
| WO | WO 03/043572 A2 | 5/2003 |
| WO | WO 03/045391 A1 | 6/2003 |
| WO | 03/072026 | 9/2003 |
| WO | WO 03/072026 | 9/2003 |
| WO | 03/089602 | 10/2003 |
| WO | WO 03/103584 A2 | 12/2003 |

OTHER PUBLICATIONS

Chollet, et al, "Development of a Topically Active Imiquimod Formulation", *Pharmaceutical Development and Technology*, 4(1), pp. 35-43 (1999).

Brassard et al.; "Interferon-α as an immunotherapeutic protein"; Journal of Leukocyte Biology; vol. 71; Apr. 2002; pp. 565-581.

Izumi et al.; "1H-imidazo[4,5-c]quinoline Derivatives as Novel Potent TNF-α Suppressors: Synthesis and Structure-Activity Relationship of 1-, 2-and 4-Substituted 1H-imidazo[4,5-c]quinolines or 1H-imidazo[4,5-c]pyridines"; *Bioorganic and Medicinal Chemistry*, vol. 11. pp. 2541-2550 (2003).

Rachkova et al., "Free Radical Production, Immunosuppression and the Role of Tyrosinase in Melanoma Genesis and Metastasis", *Periodicum Biologorum*, 1999, vol. 101, No. 3, pp. 187-192.

Akira et al., "Toll-like receptors: critical proteins linking innate and acquired immunity", *Nature Immunology*, Aug. 2001, vol. 2, No. 8; pp. 675-680.

Akira S. et al., "Recognition of pathogen-associated molecular patterns by TLR family", *Immunology Letters*, 2003, vol. 85, pp. 85-95.

Gorden et al., "Synthetic TLR Agonists Reveal Functional Differences between Human TLR7 and TLR8", *The Journal of Immunology*, 2005, vol. 174, pp. 1259-1268.

Heil et al.; "Synthetic immunostimulatory compounds activate immune cells via TLR7 and TLR8"; 33th Annual Meeting of the Deutsche Gessellschaft fürr Immunologie, Marburg 2002—Abstract C.6.

Hemmi et al., "Small anti-viral compounds activate immune cells via the TLR7 MyD88-dependent Signaling pathway", *Nature Immunology*, vol. 3, No. 2; Feb. 2002; pp. 196-200.

Hornung et al., "Quantitative Expression of Toll-Like Receptor 1-10 mRNA in Cellular Subsets of Human Peripheral Blood Mononuclear Cells and Sensitivity to CpG Oligodeoxynucleotides[1] ", *The Journal of Immunology*, 2002, 168; pp. 4531-4537.

Jurk et al. "Human TLR7 and TLR8 independently confer responsiveness to the antiviral compound R-848", *Nature Immunology*, Jun. 2002, vol. 3, No. 6; p. 1.

Medzhitov, "Toll-Like Receptors and Innate Immunity", *Nature Reviews Immunology*, vol. 1; Nov. 2001, pp. 135-145.

Ozinsky A. et al., "The repertoire for pattern recognition of pathogens by the innate immune system is defined by cooperation between Toll-like receptors" *Proc. Nat. Acad. Sci.* Dec. 2000, vol. 97, No. 25, pp. 13766-13771.

Sauder et al., "Randomized, Single-Blind, Placebo-Controlled Study of Topical Application of the Immune Response Modulator Resiquimod in Healthy Adults", *Antimicrobial Agents and Chemotherapy*, Dec. 2003, vol. 47, No. 12, pp. 3846-3852.

Hengge U. et al: "Topical immunomodulators-progress towards treating inflammation, infection, and cancer" Lancet infectious Diseases, Elsevier Ltd, US, vol. 1, No. 3, Oct. 1, 2001, pp. 189-198, XP004812198, ISSN: 1473-3099.

Wu S. J. et al: "Recent Advances in Dermatology" Clinics in Podiatric Medicine and Surgery; Saunders, Philadelphia, PA, US, vol. 19, No. 1, Jan. 1, 2002, pp. 65-78, XP008078786, ISSN: 0891-8422.

Kays Kaidbey et al: "Safety studies of topical imiquimod 5% cream on normal skin exposed to ultraviolet radiation" Toxicology, Limerick, IR, vol. 178, Sep. 2, 2002, pp. 175-182, XP002434145, ISSN: 0300-483X.

McGillis S. T. et al: "Topical treatment strategies for non-melanoma skin cancer and precursor lesions" Seminars in Cutaneous Medicine and Surgery, W.B. Saunders, Philadelphia, US, vol. 23, No. 3, Sep. 1, 2004; pp. 174-183, XP004666317, ISSN: 1085-5629.

Hengge U et al.: "Topical Immunomodulators-progress towards treating inflammation, infection, and cancer" Lancet Infectious Diseases,, Elsevier Ltd, US, vol. 1, No. 3, Oct. 1, 2001, pp. 189-198, XP004812198 ISSN: 1473-3099.

Wu S et al.: "Recent Advances in Dermatology" Clinics in Podiatric Medicine and Surgery, Saunders, Philadelphia, PA, US, vol 19, No. 1, Jan. 1, 2002, pp. 65-78, XP008076786 ISSN: 0891-8422.

Kays Kadibey et al: "Safety studies of topical imiquimod 5% cream on normal skin exposed to ultraviolet radiation" Toxicology, Limerick, IR, vol. 178, Sep. 2, 2002, pp. 175-182, XP002434145 ISSN: 0300-483X.

McGillis S T et al: "Topical treatment strategies for non-melanoma skin cancer and precursor lesions" Seminars in Cutaneous Medicine and Surgery, W.B. Saunders, Philadelphia, US, vol. 23, No. 3, Sep. 1, 2004, pp. 174-183, XP004666317 ISSN: 1085-5629.

Imiquimod Enhances the Systemic Immunity Attained by Local Cryosurgery Destruction of Melanoma Lesion, by Pedro Redondo, et al., Journal of Investigative Dermatology (2007), vol. 127, pp. 1673-1680.

Topical Imiquimod Treatment of Lentigo Maligna, by F. Ventura et al., Case Reports in Dermatology, 2009;1:78-81.

* cited by examiner

PROPHYLACTIC TREATMENT OF UV-INDUCED EPIDERMAL NEOPLASIA

CROSS-REFERENCE TO RELATED APPLICATION

This application claims priority to U.S. Provisional Patent Application No. 60/451,699, filed Mar. 4, 2003.

BACKGROUND

Solar radiation consists of a mixture of ultraviolet (UV) wavelengths including UVA wavelengths (about 315 nm to about 400 nm) and UVB wavelengths (about 280 nm to about 315 nm). Absorption of UV radiation by proteins and DNA increases toward the shorter wavelengths in the UVB range, as do the corresponding damaging effects of UV radiation to these molecules. UV-induced damage to DNA can give rise to neoplasia in UV-exposed tissues.

Neoplasia refers to the formation of one or more neoplasms. A neoplasm generally refers to an abnormal mass or colony of cells produced by a relatively autonomous new growth of tissue. Most neoplasms arise from the clonal expansion of a single cell that has undergone neoplastic transformation. Chemical, physical, or biological agents or events (e.g., exposure to UV radiation) can directly and irreversibly alter the genome of a cell, thereby transforming the cell to a neoplastic cell. Neoplastic cells are characterized by the loss of some specialized functions and the acquisition of new biological properties, foremost, the property of relatively uncontrolled growth. Cancer is a generic term for malignant neoplasms.

UV radiation can act as a complete carcinogen, i.e., capable, alone, of inducing neoplastic changes in cells. Alternatively, UV radiation can act as a co-carcinogen, acting in combination with one or more tumor initiators or promoters to induce neoplastic changes in cells.

The skin can be divided into two main layers: an outer layer—the epidermis—and the underlying dermis. The epidermis contains a basal germinative cell layer, proliferation of which provides cells for the continual renewal of the epidermis that is required as dead cells of the epidermal surface are sloughed off. While UV radiation can cause DNA damage to cells of both the dermis and the epidermis, the proliferative activity and high UV absorption of the epidermis can make the epidermis particularly susceptible to UV-related carcinogenesis.

UV radiation has been associated with various forms of epidermal damage including but not limited to erythema (sunburn) and DNA damage, which can lead to epidermal neoplasia. Various forms of epidermal neoplasia can be induced by UV radiation. For example, actinic keratosis (AK), pre-AK lesions, squamous cell carcinoma (SCC), basal cell carcinoma (BCC), and malignant melanoma can be induced by UV radiation.

Actinic keratosis is the most frequently observed form of UV-induced epidermal neoplasia. AK lesions are premalignant lesions considered to be either carcinoma in situ or squamous intraepidermal neoplasia. In humans, AK often occurs in those with fair skin and/or red hair, and those having substantial exposure to the sun early in life. Incidence of AK tends to increase with the age of the population being considered. The prevalence of AK tends to be higher in countries with high UV radiation and a fair-skinned population than in countries with a low level of UV radiation or a relatively dark-skinned population. If left untreated, AK can develop into SCC.

Melanoma and nonmelanoma skin cancers are among the most common types of cancer in Caucasian populations. Many epidemiological studies have demonstrated that the incidence of skin cancer has been increasing rapidly over the last decades.

Malignant melanoma is the most aggressive and life-threatening skin cancer. It develops in melanocytes—cells of the basal germinative cell layer of the epidermis that give the skin its color—and often spreads to other parts of the body. Incidence of malignant melanoma is closely associated with skin color and geography. Incidence among dark-skinned populations is about 1 per 100,000 population per year or less, but can be more than 50-fold greater among light-skinned populations in some areas of the world. The highest incidence rates have been reported in Queensland, Australia, with 56 new cases per 100,000 population per year for men and 43 new cases per 100,000 population per year for women. In the United States, incidence of melanoma has been estimated to be 14 new cases per year per 100,000 Caucasian men, and about 11 new cases per year per 100,000 Caucasian women.

Sun exposure, i.e., exposure to solar UV radiation, has been reported to be a general risk factor for melanoma. A more specific risk factor for melanoma is sun exposure during childhood, especially when the childhood history of exposure to solar UV radiation includes frequent or severe sunburn.

An additional risk factor for melanoma is skin type. Skin type I or II—skin that burns easily or severely and tans minimally or not at all—and the presence of multiple moles are important melanoma-related risk factors. Also, skin that is infrequently or only intermittently exposed to the sun (e.g., the skin of those who work indoors) may have a higher tendency to develop melanoma when intensely exposed to UV radiation than skin that is more regularly exposed to sunlight (e.g., the skin of those who work or are often outdoors).

Nonmelanoma skin cancers (NMSCs) constitute more than one-third of all cancers in the United States with an estimated incidence of over 600,000 cases per year. NMSCs are the most common malignancies occurring in the Caucasian population each year. Of these, most are basal cell carcinomas (BCCs) and squamous cell carcinomas (SCCs).

BCC represents 75% of NMSC and is the most common malignant disease throughout the world. There is an increased risk of NMSC in Caucasian populations, especially those who have blue eyes, a fair complexion, sunburn easily, suntan poorly, freckle with sun exposure, and/or have red, blond, or light-brown hair. NMSC is uncommon in blacks, Asians, and Hispanics. The incidence of NMSC is increasing rapidly in Caucasian populations of Europe, the United States, Canada, and Australia.

Chronic exposure to solar UV radiation is considered to be an important contributing factor to the development of NMSC. Over 80% of NMSCs occur on areas of the body that are frequently exposed to sunlight, such as the head, the neck, and the back of the hands. Additionally, BCC is also commonly found on the nose. The incidence of NMSC is elevated in individuals with a high cumulative exposure to UV light, such as those who work outdoors and those who more frequently participate in outdoor activities.

BCC is the most common skin cancer in humans. It often occurs on sun-exposed areas of the skin. It develops in the basal germinative cell layer of the epidermis. BCC can be very destructive and disfiguring, but rarely spread to other parts of the body.

SCC is a skin cancer arising from cells of the epidermis—the top layer of the skin—and can spread to other parts of the body. Squamous cell carcinoma occurs when abnormal cells—keratinocytes—of the epidermis migrate to and invade the underlying dermis.

SUMMARY

It has been found that certain small molecule IRMs can be used as a prophylactic treatment for providing protection against epidermal neoplasia such as, for example, actinic keratosis, pre-actinic keratosis lesions, malignant melanoma, and NMSCs such as, for example, basal cell carcinoma, and squamous cell carcinoma.

Accordingly, the present invention provides a method of protecting a subject against UV-induced epidermal neoplasia. Generally, the method includes administering to a subject an IRM compound in an amount effective to provide protection against UV-induced epidermal neoplasia.

In some embodiments, the IRM compound may be administered to the subject in a dose of from about 10 µg/kg to about 5 mg/kg.

In some embodiments, the IRM compound may be administered intermittently, for example, at least once per month, at least once per week, or at least twice per week. Also, in various embodiments, the treatment can begin before, simultaneously with, or after, UV exposure.

In some embodiments, the method provides protection against melanoma, basal cell carcinoma, squamous cell carcinoma, actinic keratosis, or pre-actinic keratosis lesions.

In some embodiments, the IRM compound is administered in a topical formulation. In certain embodiments, the formulation includes from about 0.01% to about 10% IRM compound, by weight. In certain embodiments, the topical formulation can be a cream, an ointment, an aerosol formulation, a non-aerosol spray, a gel, or a lotion. In some embodiments, the topical formulation may include at least one sunscreen agent.

Various other features and advantages of the present invention should become readily apparent with reference to the following detailed description, examples, and claims. In several places throughout the specification, guidance is provided through lists of examples. In each instance, the recited list serves only as a representative group and should not be interpreted as an exclusive list.

DETAILED DESCRIPTION OF ILLUSTRATIVE EMBODIMENTS OF THE INVENTION

The present invention provides a method of protecting a subject from UV-induced epidermal neoplasia by prophylactically treating the skin of the subject with an IRM compound. The present invention also provides compositions that include an IRM compound in an amount effective to provide protection against UV-induced epidermal neoplasia.

Epidermal neoplasia such as, for example, actinic keratosis, pre-actinic keratosis lesions, malignant melanoma, basal cell carcinoma, and squamous cell carcinoma, often can be the result of damage induced by exposure of the skin to UV solar radiation. Currently, protection from UV-induced skin damage is provided by the topical application of suncreens that block or screen the skin from at least a portion of the solar UV radiation spectrum. Typically, a sunscreen provides only temporary protection, it must be reapplied each time protection is sought and can provide protection only while applied to a subject. Thus, protection from UV radiation offered by sunscreens may be prematurely and/or unknowingly limited if the sunscreen is removed such as by, for example, contact with another surface, water, or perspiration.

Certain small molecule IRMs, however, can be used as a prophylactic treatment that can protect a subject against epidermal neoplasia. In contrast to the protection offered by sunscreens, protection from UV-induced epidermal neoplasia provided by certain IRM compounds can be observed when the compound is administered before or, after the subject is exposed to UV radiation. Protection also can be observed from intermittent—less than once per day—administration even when UV exposure occurs daily. Thus, in contrast to sunscreens, certain IRM compounds can provide protection against UV-induced epidermal neoplasia even on days when the IRM compound is not administered. Finally, and again in contrast to sunscreens, certain IRM compounds can continue to provide protection against epidermal neoplasia even after the compound is removed from the treatment site. Thus, the present invention provides an alternative option for prophylactic treatment against UV-induced skin damage for those who, for example, experience chronic sun exposure but cannot always conveniently apply or reapply sunscreen.

As used herein, "protect" and variations thereof refer to any measurable reduction in the likelihood, occurrence, and/or severity (e.g., number and/or size) of epidermal neoplastic lesions.

The method of the invention may be employed to decrease the likelihood, occurrence, and/or severity of epidermal neoplasia in a subject that has not yet exhibited clinical evidence of a condition for which epidermal neoplasia is a symptom (e.g., BCC, SCC, melanoma, etc.). Thus, in some embodiments, the method may protect a subject from a first instance of epidermal neoplasia. In other embodiments, the method may protect a subject from the growth or spread of subclinical epidermal neoplastic lesions.

Alternatively, the method may be employed to decrease the likelihood and/or severity of epidermal neoplasia recurrence in a subject that has received treatment for clinically evident epidermal neoplasia. As used herein, "recurrence" and variations thereof refer to reappearance of epidermal neoplasia after apparent clearance of treated epidermal neoplastic lesions, without regard to the underlying mechanism of the recurrence (i.e., whether recurrence occurs because, for example, the initial lesions were incompletely cleared, or the subject possesses one or more genetic or environmental risk factors for developing epidermal neoplasia) or the manner in which initial epidermal neoplastic lesions were treated (e.g., surgery, chemotherapy, immunotherapy, etc.). Thus, in some embodiments, the method may be used to protect a subject from recurring instances of epidermal neoplasia.

Immune response modifier compounds ("IRMs") include compounds that possess potent immunomodulating activity including but not limited to antiviral and antitumor activity. Certain IRMs modulate the production and secretion of cytokines. For example, certain IRM compounds induce the production and secretion of cytokines such as, e.g., Type I interferons, TNF-α, IL-1, IL-6, IL-8, IL-10, IL-12, MIP-1, and/or MCP-1. As another example, certain IRM compounds can inhibit production and secretion of certain $T_H2$ cytokines, such as IL-4 and IL-5. Additionally, some IRM compounds are said to suppress IL-1 and TNF (U.S. Pat. No. 6,518,265).

Certain IRMs are small organic molecules (e.g., molecular weight under about 1000 Daltons, preferably under about 500 Daltons, as opposed to large biological molecules such as proteins, peptides, and the like) such as those disclosed in, for example, U.S. Pat. Nos. 4,689,338; 4,929,624; 4,988,815; 5,037,986; 5,175,296; 5,238,944; 5,266,575; 5,268,376; 5,346,905; 5,352,784; 5,367,076; 5,389,640; 5,395,937; 5,446,153; 5,482,936; 5,693,811; 5,741,908; 5,756,747; 5,939,090; 6,039,969; 6,083,505; 6,110,929; 6,194,425;

6,245,776; 6,331,539; 6,376,669; 6,451,810; 6,525,064; 6,541,485; 6,545,016; 6,545,017; 6,558,951; 6,573,273; 6,656,938; 6,660,735; 6,660,747; 6,664,260; 6,664,264; 6,664,265; 6,667,312; 6,670,372; 6,677,347; 6,677,348; 6,677,349; 6,683,088; European Patent 0 394 026; U.S. Patent Publication Nos. 2002/0016332; 2002/0055517; 2002/0110840; 2003/0133913; 2003/0199538; and 2004/0014779; and International Patent Publication Nos. WO 01/74343; WO 02/46749 WO 02/102377; WO 03/020889; WO 03/043572; WO 03/045391; and WO 03/103584.

Additional examples of small molecule IRMs include certain purine derivatives (such as those described in U.S. Pat. Nos. 6,376,501, and 6,028,076), certain imidazoquinoline amide derivatives (such as those described in U.S. Pat. No. 6,069,149), certain imidazopyridine derivatives (such as those described in U.S. Pat. No. 6,518,265), certain benzimidazole derivatives (such as those described in U.S. Pat. No. 6,387,938), certain derivatives of a 4-aminopyrimidine fused to a five membered nitrogen containing heterocyclic ring (such as adenine derivatives described in U.S. Pat. Nos. 6,376,501; 6,028,076 and 6,329,381; and in WO 02/08595), and certain 3-β-D-ribofuranosylthiazolo[4,5-d]pyrimidine derivatives (such as those described in U.S. Publication No. 2003/0199461).

Other IRMs include large biological molecules such as oligonucleotide sequences. Some IRM oligonucleotide sequences contain cytosine-guanine dinucleotides (CpG) and are described, for example, in U.S. Pat. Nos. 6,194,388; 6,207,646; 6,239,116; 6,339,068; and 6,406,705. Some CpG-containing oligonucleotides can include synthetic immunomodulatory structural motifs such as those described, for example, in U.S. Pat. Nos. 6,426,334 and 6,476,000. Other IRM nucleotide sequences lack CpG and are described, for example, in International Patent Publication No. WO 00/75304.

Other IRMs include biological molecules such as aminoalkyl glucosaminide phosphates (AGPs) and are described, for example, in U.S. Pat. Nos. 6,113,918; 6,303,347; 6,525,028; and 6,649,172.

IRM compounds suitable for use in the invention include compounds having a 2-aminopyridine fused to a five membered nitrogen-containing heterocyclic ring. Such compounds include, for example, imidazoquinoline amines including but not limited to substituted imidazoquinoline amines such as, for example, amide substituted imidazoquinoline amines, sulfonamide substituted imidazoquinoline amines, urea substituted imidazoquinoline amines, aryl ether substituted imidazoquinoline amines, heterocyclic ether substituted imidazoquinoline amines, amido ether substituted imidazoquinoline amines, sulfonamido ether substituted imidazoquinoline amines, urea substituted imidazoquinoline ethers, thioether substituted imidazoquinoline amines, and 6-, 7-, 8-, or 9-aryl or heteroaryl substituted imidazoquinoline amines; tetrahydroimidazoquinoline amines including but not limited to amide substituted tetrahydroimidazoquinoline amines, sulfonamide substituted tetrahydroimidazoquinoline amines, urea substituted tetrahydroimidazoquinoline amines, aryl ether substituted tetrahydroimidazoquinoline amines, heterocyclic ether substituted tetrahydroimidazoquinoline amines, amido ether substituted tetrahydroimidazoquinoline amines, sulfonamido ether substituted tetrahydroimidazoquinoline amines, urea substituted tetrahydroimidazoquinoline ethers, and thioether substituted tetrahydroimidazoquinoline amines; imidazopyridine amines including but not limited to amide substituted imidazopyridine amines, sulfonamide substituted imidazopyridine amines, urea substituted imidazopyridine amines, aryl ether substituted imidazopyridine amines, heterocyclic ether substituted imidazopyridine amines, amido ether substituted imidazopyridine amines, sulfonamido ether substituted imidazopyridine amines, urea substituted imidazopyridine ethers, and thioether substituted imidazopyridine amines; 1,2-bridged imidazoquinoline amines; 6,7-fused cycloalkylimidazopyridine amines; imidazonaphthyridine amines; tetrahydroimidazonaphthyridine amines; oxazoloquinoline amines; thiazoloquinoline amines; oxazolopyridine amines; thiazolopyridine amines; oxazolonaphthyridine amines; thiazolonaphthyridine amines; imidazoquinoline-1,4-diamines; and 1H-imidazo dimers fused to pyridine amines, quinoline amines, tetrahydroquinoline amines, naphthyridine amines, or tetrahydronaphthyridine amines.

In one embodiment, the IRM may be an imidazoquinoline amine such as, for example, 1-(2-methylpropyl)-1H-imidazo[4,5-c]quinolin-4-amine or 4-amino-α,α-dimethyl-2-ethoxymethyl-1H-imidazo[4,5-c]quinolin-1-ethanol.

In certain embodiments, the IRM compound may be an imidazonaphthyridine amine, a tetrahydroimidazonaphthyridine amine, an oxazoloquinoline amine, a thiazoloquinoline amine, an oxazolopyridine amine, a thiazolopyridine amine, an oxazolonaphthyridine amine, or a thiazolonaphthyridine amine.

In certain embodiments, the IRM compound may be a substituted imidazoquinoline amine, a tetrahydroimidazoquinoline amine, an imidazopyridine amine, a 1,2-bridged imidazoquinoline amine, a 6,7-fused cycloalkylimidazopyridine amine, an imidazonaphthyridine amine, a tetrahydroimidazonaphthyridine amine, an oxazoloquinoline amine, a thiazoloquinoline amine, an oxazolopyridine amine, a thiazolopyridine amine, an oxazolonaphthyridine amine, or a thiazolonaphthyridine amine.

As used herein, a substituted imidazoquinoline amine refers to an amide substituted imidazoquinoline amine, a sulfonamide substituted imidazoquinoline amine, a urea substituted imidazoquinoline amine, an aryl ether substituted imidazoquinoline amine, a heterocyclic ether substituted imidazoquinoline amine, an amido ether substituted imidazoquinoline amine, a sulfonamido ether substituted imidazoquinoline amine, a urea substituted imidazoquinoline ether, a thioether substituted imidazoquinoline amines, or a 6-, 7-, 8-, or 9-aryl or heteroaryl substituted imidazoquinoline amine. As used herein, substituted imidazoquinoline amines specifically and expressly exclude 1-(2-methylpropyl)-1H-imidazo[4,5-c]quinolin-4-amine and 4-amino-α,α-dimethyl-2-ethoxymethyl-1H-imidazo[4,5-c]quinolin-1-ethanol.

In some embodiments, suitable IRM compounds also may include the purine derivatives, small heterocyclic compounds, amide derivatives, and oligonucleotide sequences described above. In some embodiments, the IRM compound may be a compound identified as an agonist of one or more Toll-like receptors (TLRs). Certain small molecule IRM compounds have been identified as agonists of one or more of TLR6, TLR7, and TLR8. Certain oligonucleotide IRM compounds have been identified as agonists of TLR9.

In one particular embodiment, the IRM compound is an imidazonaphthyridine amine such as, for example, 1-(2-methylpropyl)-1H-imidazo[4,5-c][1,5]naphthyridin-4-amine or 2-methyl-1-(2-methylpropyl)-1H-imidazo[4,5-c][1,5]naphthyridin-4-amine.

In an alternative embodiment, the IRM compound is a 1,2-bridged imidazoquinoline amine such as, for example, 8,9,10,11-tetrahydropyrido[1',2':1,2]imidazo[4,5-c]quinolin-6-amine.

In another alternative embodiment, the IRM compound is an amide substituted imidazoquinoline amine such as, for example, N-{2-[4-amino-2-(ethoxymethyl)-1H-imidazo[4,5-c]quinolin-1-yl]-1,1-dimethylethyl}cyclohexanecarboxamide or N-[4-(4-amino-2-ethyl-1H-imidazo[4,5-c]quinolin-1-yl)butyl]-2-methylpropanamide.

In another alternative embodiment, the IRM compound is a sulfonamide substituted imidazoquinoline amine such as, for example, N-[2-(4-amino-2-propyl-1H-imidazo[4,5-c]quinolin-1-yl)-1,1-dimethylethyl]methanesulfonamide.

In another alternative embodiment, the IRM compound is a sulfonamide substituted tetrahydroimidazoquinoline amine such as, for example, N-{2-[4-amino-2-(2-methoxyethyl)-6,7,8,9-tetrahydro-1H-imidazo[4,5-c]quinolin-1-yl]-1,1-dimethylethyl} methanesulfonamide.

In another alternative embodiment, the IRM compound is a urea substituted imidazoquinoline amine such as, for example, N-[4-(4-amino-2-propyl-1H-imidaz[4,5-c]quinolin-1-yl)butyl]-N'-isopropylurea.

In another alternative embodiment, the IRM compound is an imidazopyridine amine such as, for example, N-{2-[4-amino-2-(ethoxymethyl)-6,7-dimethyl-1H-imidazo[4,5-c]pyridin-1-yl]-1,1-dimethylethyl}-N'-cyclohexylurea.

In another alternative embodiment, the IRM compound is a heterocyclic ether substituted imidazoquinoline amine such as, for example, 1-{2-[3-(3-pyridyl)propoxy]ethyl}-1H-imidazo[4,5-c]quinolin-4-amine.

In another alternative embodiment, the IRM compound is a thioether substituted imidazoquinoline amine such as, for example, 2-butyl-1-[3-(methylsulfonyl)propyl]-1H-imidazo[4,5-c]quinolin-4-amine or 2-butyl-1-[2-(propylsulfonyl)ethyl]-1H-imidazo[4,5-c]quinolin-4-amine.

In yet another alternative embodiment, the IRM compound is an imidazoquinoline-1,4-diamine such as, for example, 2-ethoxymethyl-$N^1$-isopropyl-1H-imidazo[4,5-c]quinoline-1,4-diamine.

Unless otherwise indicated, reference to a compound can include the compound in any pharmaceutically acceptable form, including any isomer (e.g., diastereomer or enantiomer), salt, solvate, polymorph, and the like. In particular, if a compound is optically active, reference to the compound can include each of the compound's enantiomers as well as racemic mixtures of the enantiomers.

The IRM compound may be provided in a formulation suitable for topical administration. Suitable types of formulations are described, for example, in International Patent Publication No. WO 03/045391. The IRM compound may be provided in any suitable form including but not limited to a solution, a suspension, an emulsion, or any form of mixture. The IRM may be delivered in formulation with any pharmaceutically acceptable excipient, carrier, or vehicle. The formulation may be delivered in any conventional topical dosage form such as, for example, a cream, an ointment, an aerosol formulation, a non-aerosol spray, a gel, a lotion, and the like. The formulation may further include one or more additives including but not limited to adjuvants, skin penetration enhancers, colorants, fragrances, moisturizers, thickeners, and the like. In some embodiments, the IRM compound may be provided in a formulation with one or more sunscreen agents.

Sunscreen agents can include agents that block at least a portion of UVB and/or UVA solar radiation. Some sunscreen agents may preferentially block UVB radiation. Other sunscreen agents may preferentially block UVB radiation. Still other sunscreen agents may block UVA and UVB radiation. Suitable sunscreen agents include, for example, aminobenzoic acid, p-aminobenzoic acid (PABA), padimate O, homosalate, octyl methoxycinnamate, benzophenone, octyl salicylate, trolamine salicylate, phenylbenzimidazole, sulisobenzone, aminobenzoic acid, sulfonic acid, octocrylene, oxybenzone, dioxybenzone, avobenzone, titanium dioxide, zinc oxide, lisadimate, roxadimate, menthyl anthranilate, benzoate-4 methylbenzylidene camphor, and mexoryl SX.

In some embodiments, the methods of the present invention include administering an IRM compound to a subject in a formulation of, for example, from about 0.0001% to about 10% (unless otherwise indicated, all percentages provided herein are weight/weight with respect to the total formulation) to the subject, although in some embodiments the IRM compound may be administered using a formulation that provides IRM compound in a concentration outside of this range. In certain embodiments, the method includes administering to a subject a formulation that includes from about 0.01% to about 1% IRM compound, for example, a formulation that includes about 0.1% IRM compound.

An amount of an IRM compound effective for providing protection against UV-induced epidermal neoplasia is an amount sufficient to reduce the size, the frequency of occurrence, or both, of UV-induced epidermal neoplasia in a subject or a portion of a subject. The precise amount of IRM compound for providing protection against UV-induced neoplasia will vary according to factors known in the art including but not limited to the physical and chemical nature of the IRM compound, the formulation in which the IRM compound is provided, the nature of the carrier, the intended dosing regimen, the state of the subject's immune system (e.g., suppressed, compromised, stimulated), the method of administering the IRM compound, and the species to which the formulation is being administered. Accordingly it is not practical to set forth generally the amount that constitutes an amount of IRM compound effective to provide protection against UV-induced epidermal neoplasia for all possible applications. Those of ordinary skill in the art, however, can readily determine the appropriate amount with due consideration of such factors.

The precise amount of IRM compound will vary according to factors known in the art. In some embodiments, an amount of IRM compound effective for providing protection against UV-induced epidermal neoplasia is an amount sufficient to provide a dose of about 100 ng/kg to about 50 mg/kg, although in some embodiments an effective amount of IRM compound may be provided in a dose outside this range. In certain embodiments, an amount of IRM compound effective for providing protection against UV-induced epidermal neoplasia may be an amount of IRM compound that provides a dose of from about 10 µg/kg to about 5 mg/kg, for example, from about 100 µg/kg to about 1 mg/kg.

The dosing regimen may depend at least in part on many factors known in the art including but not limited to the physical and chemical nature of the IRM compound, the nature of the carrier, the amount of IRM being administered, the state of the subject's immune system (e.g., suppressed, compromised, stimulated), the frequency, duration, and/or intensity of UV exposure, the method of administering the IRM compound, and the species to which the formulation is being administered. Accordingly it is not practical to set forth generally the dosing regimen effective to provide protection against UV-induced epidermal neoplasia for all possible applications. Those of ordinary skill in the art, however, can readily determine the appropriate amount with due consideration of such factors.

More frequent administration of the IRM compound, even if at lower doses, may provide more continuous (i.e., uninterrupted) protection against UV-induced epidermal neoplasia.

Such dosing regimens may be desirable, for example, for subjects at high risk of developing epidermal neoplasia. Such dosing regimens also may be desirable, for example, for those in geographic locations having sustained and/or intense exposure to UV radiation.

Less frequent administration may provide less continuous (i.e., interrupted) protection against UV-induced epidermal neoplasia. Such dosing regimens may be sufficient for those, for example, in geographic locations (e.g., higher latitudes) that experience periods of decreased solar UV radiation intensity.

In some embodiments of the invention, the IRM compound may be administered, for example, from about twice per day to about once per month, although in some embodiments the methods of the present invention may be performed by administering the IRM compound at a frequency outside this range. In addition, the IRM compound may be administered on a regular, recurring, or scheduled basis. Alternatively, the IRM compound may be administered on an irregular schedule—i.e., at varying intervals such as, for example, when exposure to UV radiation is expected and/or has already occurred.

In certain embodiments, the IRM compound may be administered from about once per week to about seven times per week. In one particular embodiment, the IRM compound is administered twice per week. Treatment methods according to the present invention may be initiated after, concurrent with, or before exposure to UV radiation.

In one particular embodiment, a formulation that includes an IRM compound may be administered to one at risk for developing epidermal neoplasia. Such individuals may possess one or more risk factors such as, for example, previously diagnosis of and/or treatment for epidermal neoplasia, age, present extent (e.g., frequency, duration, and/or intensity) of UV exposure, childhood history of UV exposure, sunburn history, skin type, possessing multiple moles, hair color, eye color, etc. Treatment may involve all or a portion of sun-exposed areas of the skin. For example, treatment may be limited to areas of relatively high UV exposure such as, for example, the scalp, face (including e.g., the ears and nose), neck, arms, legs, and hands. In some cases, the IRM compound may be applied to an area that has previously received treatment for prior epidermal neoplasia such as, for example, a skin graft or other site from which a neoplastic lesion has been removed.

In another particular embodiment, the IRM compound may be provided as an additive to a conventional skincare product such as, for example, sunscreen, moisturizing lotion, or cosmetic (e.g., a face cream or make-up). Consequently, the IRM compound may be administered when a subject applies the skincare product. In such cases, the dosing regimen may be subject to the schedule of use for the skincare product.

In the case in which the IRM compound is an additive to a sunscreen product, the IRM compound may provide protection against epidermal neoplasia induced by exposure to UV radiation that occurs over a greater period of time than can be protected against by the sunscreen alone. For example, the IRM compound may provide protection against epidermal neoplasia induced by exposure to UV radiation that occurred prior to application of the sunscreen/IRM product or occurs after the sunscreen/IRM product is removed from the skin (e.g., by washing, perspiration, etc.).

In the case in which the IRM compound is an additive to, for example, a moisturizing lotion or cosmetic, the IRM compound may be administered more frequently. Consequently, a lower dose of IRM may be sufficient to provide protection against UV-induced epidermal neoplasia.

The methods of the present invention may be performed on any suitable subject. Suitable subjects include but are not limited to animals such as but not limited to humans, non-human primates, rodents, dogs, cats, horses, pigs, sheep, goats, or cows.

EXAMPLES

The following examples have been selected merely to further illustrate features, advantages, and other details of the invention. It is to be expressly understood, however, that while the examples serve this purpose, the particular materials and amounts used as well as other conditions and details are not to be construed in a matter that would unduly limit the scope of this invention.

IRM Compounds

The IRM compounds used in the examples are shown in Table 1.

TABLE 1

| Compound | Chemical Name | Reference |
| --- | --- | --- |
| IRM1 | 1-(2-methylpropyl)-1H-imidazo[4,5-c][1,5]naphthyridin-4-amine | U.S. Pat. No. 6,194,425 Example 32 |
| IRM2 | 2-methyl-1-(2-methylpropyl)-1H-imidazo[4,5-c][1,5]naphthyridin-4-amine | U.S. Pat. No. 6,194,425 Example 36 |
| IRM3 | 8,9,10,11-tetrahydropyrido[1',2':1,2]imidazo[4,5-c]quinolin-6-amine | U.S. Pat. No. 5,482,936 Example 1 |
| IRM4 | N-{2-[4-amino-2-(ethoxymethyl)-1H-imidazo[4,5-c]quinolin-1-yl]-1,1-dimethylethyl}cyclohexanecarboxamide | U.S. Pat. No. 2003/0144283[#] |
| IRM5 | N-[4-(4-amino-2-ethyl-1H-imidazo[4,5-c]quinolin-1-yl)butyl]-2-methylpropanamide | U.S. Pat. No. 2003/0144283 Example 199 |
| IRM6 | N-[2-(4-amino-2-propyl-1H-imidazo[4,5-c]quinolin-1-yl)-1,1-dimethylethyl]methanesulfonamide | U.S. Pat. No. 6,677,349[#] |
| IRM7 | N-{2-[4-amino-2-(2-methoxyethyl)-6,7,8,9-tetrahydro-1H-imidazo[4,5-c]quinolin-1-yl]-1,1-dimethylethyl}methanesulfonamide | U.S. Pat. No. 6,331,539[#] |
| IRM8 | N-[4-(4-amino-2-propyl-1H-imidazo[4,5-c]quinolin-1-yl)butyl]-N'-isopropylurea | U.S. Pat. No. 6,541,485[#] |
| IRM9 | N-{2-[4-amino-2-(ethoxymethyl)-6,7-dimethyl-1H-imidazo[4,5-c]pyridin-1-yl]-1,1-dimethylethyl}-N'-cyclohexylurea | U.S. Pat. No. 6,545,017[#] |

TABLE 1-continued

| Compound | Chemical Name | Reference |
|---|---|---|
| IRM10 | 1-{2-[3-(3-pyridyl)propoxy]ethyl}-1H-imidazo[4,5-c]quinolin-4-amine | WO 02/46193 Example 33 |
| IRM11 | 2-butyl-1-[3-(methylsulfonyl)propyl]-1H-imidazo[4,5-c]quinolin-4-amine | U.S. Pat. No. 6,664,264 Example 19 |
| IRM12 | 2-butyl-1-[2-(propylsulfonyl)ethyl]-1H-imidazo[4,5-c]quinolin-4-amine | U.S. Pat. No. 6,667,312 Example 62 |
| IRM13 | 2-ethoxymethyl-$N^1$-isopropyl-1H-imidazo[4,5-c]quinoline-1,4-diamine | U.S. Ser. No. 60/453128 Example 5 |
| IRM14 | 1-(2-methylpropyl)-1H-imidazo[4,5-c]quinolin-4-amine | U.S. Pat. No. 4,689,338 Example 99 |

Topical Formulations

Unless otherwise noted, the formulation of the vehicles used in the following examples, on a percentage weight-by-weight basis, is provided in Table 2.

TABLE 2

| Materials | Vehicle 1 | Vehicle 2 |
|---|---|---|
| Isopropyl Myristate, NF | 10.00 | |
| PRIPURE (Uniqema, New Castle, DE) | | 10.00 |
| Isostearic Acid | 5.00 | 5.00 |
| PLURONIC F68, NF (BASF Corp., Mount Olive, NJ) | 2.5 | 2.5 |
| Disodium EDTA, USP | 0.05 | 0.05 |
| CARBOMER 974 (CarboMer, Inc., San Diego, CA) | 1.00 | |
| CARBOMER 980 (CarboMer, Inc.) | | 0.7 |
| Propylene glycol, USP | 15.00 | |
| Diethylene Glycol Monoethyl Ether, USP | | 10.00 |
| Propylparaben, NF | 0.1 | |
| Ethylparaben, NF | | 0.2 |
| Methylparaben, NF | 0.2 | 0.2 |
| Purified water, USP | 65.65 | 70.95 |
| 20% w/w NaOH | 0.5 | 0.4 |

Formulations containing IRM compound were prepared by adding the appropriate amount of IRM compound, on a percentage weight-by-weight basis, to the vehicle to obtain the final IRM weight percentage, and decreasing the amount of water added accordingly.

The formulation was prepared as follows:

Oil phase preparation: IRM compound, when present, was dissolved in isostearic acid and either isopropyl myristate or PRIPURE, with heat if necessary. CARBOMER 974 or CARBOMER 980, as indicated, was then dispersed in the oil phase.

Water phase preparation: Disodium EDTA was dissolved in the water. Methylparaben and either propylparaben or ethylparaben, as indicated, were dissolved in either propylene glycol or diethylene glycol monoethyl ether, as indicated, and the solution was subsequently added to the water phase. PLURONIC F68 was then added to the water phase and mixed until dissolved.

Phase combination: The oil phase was added to the water phase at ambient conditions. The emulsion was then homogenized. After homogenization, sodium hydroxide solution (20% w/w) was added and the resulting cream was mixed until smooth and uniform. The pH of the cream was measured and a pH adjustment was made with additional sodium hydroxide solution, if necessary, to meet the in-process target pH of 5.0.

Animal Model:

Female SKH-1 mice 9-10 weeks old were obtained from Charles River (Raleigh, N.C.) and housed in a room with controlled temperatures and humidity and alternating 12-hour light and dark cycles. The room is lit with fluorescent lights covered by yellow sleeves from EncapSulite International, Inc. (Rosenberg, Tex.) to eliminate all ambient UV radiation. The mice were fed with a 12% Corn Oil Purified Diet from Purina Test Diet (Richmond, Va.) and water, ad libitum. The animals were maintained in facilities approved by the Association for the Assessment and Accreditation of Laboratory Animal Care International and in accordance with current United States Department of Agriculture, Department of Health and Human Services, and National Institutes of Health regulations and standards.

A small group of mice were not exposed to UV and were used as negative controls. The other mice were chronically UV irradiated. After randomization the mice were lightly anesthetized with halothane and adjustable collars made of hook and loop fastener approximately 10 mm wide and 70 mm long were placed around the mouse's neck to prevent oral ingestion of the IRM. Unless otherwise indicated, thirty minutes before UV exposure mice were topically dosed with 30 µL of either (1) vehicle formulation, (2) IRM formulation, or (3) an SPF 30 sunscreen (NEUTROGENA SPF30 Sunblock with PARSOL 1789), two times per week for a total of 15-18 weeks on the dorsal surface in an area approximately 6 cm². Approximately four hours after dosing, the topical treatment (i.e, vehicle formulation; IRM formulation, or sunscreen) was washed off using a dilute soap solution.

Mice were placed in a standard plexiglass rat cage, 9-10 at a time, that was separated into 12 individual compartments with plexiglass dividers and placed on a shelf 14 inches below the light source without wire cage tops. The mice were exposed to UV radiation 5 times per week (Monday thru Friday) for an average of 15-18 weeks. The UV radiation was provided by a bank of six FS40 lamps (National Biological Corporation, Twinsburg, Ohio), filtered by a Kodacel filter (140 µm thick K6808 cellulose triacetate film; Eastman Kodak, Rochester, N.Y.) that transmits radiation having a wavelength from about 293 nm to about 400 nm. The Kodacel filter was aged 4-6 hours before use. The lights emit UVB (21%) and UVA (79%) light with a peak wavelength of 313 nm, as measured using a radiometer Model PMA 2200 from Solar Light Company (Philadelphia, Pa.) with a PMA 2101 detector for UVB and PMA2110 detector for UVA.

The dose of UVB irradiation was measured by MED (minimal erythemal dose). By using MED, a relatively constant incident dose of UV was maintained over time. The initial dose of UVB to the mice was 12.6 mJ/cm² (0.6 MED) and the average total dose of UVB was 3000-5200 mJ/cm². An increase of 10-20% of the MED dose per week was needed due to acclimation of the mice.

All mice were distinguished from one another by a tattoo placed on the tail. The development and appearance of tumors were noted weekly and recorded starting at about 14-18 weeks.

Example 1

IRM1 and IRM2 formulations were prepared using Vehicle 1. UV dosing and IRM dosing were initiated simultaneously. UV dosing was performed five days per week for 15 weeks. Topical dosing (IRM or vehicle) was performed twice per week at the doses indicated in Table 3.

After 15 weeks, the mice were subjected to gross inspection to determine the presence of a disease state, i.e., squamous cell carcinoma (SCC), actinic keratosis (AK), or pre-AK lesions. Results are shown in Table 3 and are expressed as the percentage of mice exhibiting a disease state:

$$\% \text{ Disease} = \frac{(SCC + AK + \text{pre-}AK \text{ lesion})}{\text{Total mice}}$$

TABLE 3

| Treatment | No. of mice | % Disease |
|---|---|---|
| UV Exposed - vehicle | 10 | 70 |
| UV Exposed - 0.1% IRM1 | 10 | 0 |
| UV Exposed - 0.1% IRM2 | 9 | 11 |
| No UV exposure | 5 | 0 |

Example 2

A 0.1% formulation of IRM2 was prepared using Vehicle 1. A 1.0% formulation of IRM2 was prepared using Vehicle 1, except that the isostearic acid was increased to 13.0% (w/w), the NaOH was decreased to 0.5% (w/w), and the water was adjusted accordingly. Vehicle 2 was used as the placebo cream. UV dosing was performed for six weeks before IRM dosing was initiated. UV dosing was performed five days per week for 15 weeks. Topical dosing (IRM, vehicle, or sunscreen) was performed twice per week at the doses indicated in Table 4.

After 15 weeks, the mice were subjected to gross inspection to determine the presence of a disease state, i.e., squamous cell carcinoma (SCC), actinic keratosis (AK), or pre-AK lesions. Results are shown in Table 4.

TABLE 4

| Treatment | No. of mice | % Disease |
|---|---|---|
| UV Exposed - 0.1% IRM2 | 8 | 63 |
| UV Exposed - 1.0% IRM2 | 6 | 50 |
| UV Exposed - SPF 30 sunscreen | 8 | 63 |
| UV Exposed - vehicle | 8 | 75 |
| No UV exposure | 5 | 0 |

Example 3

Formulations of IRM1 and IRM2 were prepared using Vehicle 1. UV dosing and IRM dosing were initiated simultaneously. UV dosing was performed five days per week for 18 weeks. Topical dosing (IRM, vehicle, or sunscreen) was performed twice per week at the doses indicated in Table 6.

After 18 weeks, the mice were subjected to gross inspection to determine the presence of a disease state, i.e., squamous cell carcinoma (SCC), actinic keratosis (AK), or pre-AK lesions. Results are shown in Table 6.

The disease state of each mouse was scored by measuring the size and/or number of lesions present on the mouse. SCC lesions and AK lesions of at least 1 mm in diameter were given a score of 1. Pre-AK lesions of less than 1 mm were scored as indicated in Table 5.

TABLE 5

Scoring of UV-induced lesions less than 1 mm in diameter

| Lesion Frequency | Score |
|---|---|
| Rare (0-1) | 0 |
| Few (2-10) | 0.5 |
| Moderate (11-20) | 1.0 |
| Many (>21) | 1.5 |

The SCC lesion score, AK lesion score, and the pre-AK lesion score (according to Table 5) were added to provide a total disease score for each mouse. Table 6 includes the average disease score for all of the mice in each treatment group.

TABLE 6

| Treatment | No. of Mice | % Disease | Avg. Disease Score |
|---|---|---|---|
| UV Exposed - 0.1% IRM 2 | 8 | 25 | 0.6 ± 0.42 |
| UV Exposed - 0.01% IRM 2 | 7 | 71 | 4.86 ± 1.81 |
| UV Exposed - 0.1% IRM 1 | 6 | 50 | 0.66 ± 0.33 |
| UV Exposed - 0.01% IRM 1 | 7 | 71 | 2.86 ± 0.82 |
| UV Exposed - SPF 30 sunscreen | 5 | 40 | 0.6 ± 0.4 |
| UV Exposed - vehicle | 8 | 75 | 1.75 ± 0.53 |
| No UV exposure | 5 | 0 | 0 |

Example 4

IRM compounds were formulated as shown in Table 7. UV dosing and IRM dosing were initiated simultaneously. Daily UV dosing was performed five days per week for 17 weeks. IRM dosing was performed twice per week with the compounds indicated in Table 9, each in a 0.1% formulation. SPF dosing was performed five times per week.

TABLE 7

| Materials | w/w % |
|---|---|
| IRM compound | 0.10 |
| CRODAMOL GTCC-PN (Croda, Inc., Parsippany, NJ) | 10.00 |
| Isostearic Acid | 5.00 |
| PLURONIC F68, NF (BASF Corp., Mount Olive, NJ) | 2.5 |
| Disodium EDTA, USP | 0.05 |
| CARBOPOL 980 (Noveon, Inc., Cleveland, OH) | 0.7 |
| TRANSCUTOL P (Gattefosse Corp., Paramus, NJ) | 10.00 |
| Ethylparaben, NF | 0.2 |
| Methylparaben, NF | 0.2 |
| Purified water, USP | 70.85 |
| 20% w/w NaOH | 0.4 |

An additional group of mice were topically dosed twice per week with 0.1% formulation of a non-IRM control compound: 1,5-dihydro-1-(2-methylpropyl)-4H-imidazo[4,5-c]quinolin-4-one, the synthesis of which is described in U.S. Pat. No. 4,698,348, Example 71, formulated as shown in Table 8. The non-IRM compound is structurally related to, but outside the scope of, IRM compounds as provided above. In contrast to IRM compounds, the non-IRM compound does not induce the production and secretion of cytokines. Mice in the non-IRM group were UV dosed five times per week for 18 weeks.

TABLE 8

| Materials | w/w % |
|---|---|
| Non-IRM compound | 0.1 |
| PRIPURE (Uniqema, New Castle, DE) | 10.00 |
| Isostearic Acid | 5.00 |
| TRANSCUTOL P (Gattefosse Corp., Paramus, NJ) | 10.00 |
| PLURONIC F68, NF (BASF Corp., Mount Olive, NJ) | 2.5 |
| Disodium EDTA, USP | 0.05 |
| CARBOPOL 980, NF | 0.7 |
| Ethylparaben, NF | 0.2 |
| Methylparaben, NF | 0.2 |
| Purified water, USP | 70.85 |
| 20% w/w NaOH | 0.4 |

After the course of treatment and UV dosing, the mice were subjected to gross inspection to determine the presence of a disease state, i.e., squamous cell carcinoma (SCC), actinic keratosis (AK), or pre-AK lesions. Results are shown in Table 9.

The disease state of each mouse was scored by measuring the number of lesions present on the mouse. All SCC lesions, AK lesions, and pre-AK lesions were given a score of 1.

TABLE 9

| Treatment | No. of Mice | Diseased | % Disease | Avg. Disease Score |
|---|---|---|---|---|
| UV Exposed - IRM 3 | 10 | 3 | 30 | 1.00 ± 0.54 |
| UV Exposed - IRM 4 | 9 | 1 | 11 | 0.67 ± 0.67 |
| UV Exposed - IRM 5 | 10 | 6 | 60 | 5.40 ± 1.91 |
| UV Exposed - IRM 6 | 8 | 1 | 13 | 0.38 ± 0.38 |
| UV Exposed - IRM 7 | 10 | 6 | 60 | 3.90 ± 1.30 |
| UV Exposed - IRM 8 | 8 | 6 | 75 | 3.13 ± 0.89 |
| UV Exposed - IRM 9 | 5 | 3 | 60 | 2.00 ± 0.89 |
| UV Exposed - IRM 10 | 10 | 7 | 70 | 2.50 ± 1.07 |
| UV Exposed - IRM 11 | 10 | 2 | 20 | 0.70 ± 0.47 |
| UV Exposed - IRM 12 | 9 | 0 | 0 | 0.00 ± 0.00 |
| UV Exposed - IRM 13 | 6 | 4 | 67 | 3.33 ± 1.54 |
| UV Exposed - sunscreen | 8 | 0 | 0 | 0.00 ± 0.00 |
| UV Exposed - vehicle | 9 | 9 | 100 | 12.22 ± 2.04 |
| UV Exposed - non-IRM | 8 | 7 | 88 | 10.25 ± 2.06 |
| No UV exposure | 5 | 0 | 0 | 0.00 ± 0.00 |

Example 5

Subjects with four to eight clinically typical, visible, discrete actinic keratosis (AK) lesions in a 25 cm² treatment area were randomized in a 1:1 ratio to receive either a 5% cream formulation of IRM14 (ALDARA, 3M Company, St. Paul, Minn.) or vehicle cream once daily three days per week. Subjects received treatment for sixteen weeks even if clinical evidence of lesion clearance was observed. Subjects were evaluated at an Evaluation visit eight weeks after the treatment period concluded.

Subjects were instructed to administer a single application of cream (vehicle or IRM14, as assigned) to the treatment area at approximately the same time of day three days per week. The subjects were instructed to wash the treatment area prior to applying the cream, rub the cream into the treatment area, and then leave the cream in place for at least eight hours without occlusion.

Subjects with no (zero) clinically visible AK lesions in the 25 cm² treatment area at the Evaluation visit were considered complete responders. 117 of 242 (48.3%) subjects receiving IRM14 were complete responders; 18 of 250 (7.2%) vehicle-treated subjects were complete responders.

Complete responders were re-evaluated for recurrence of AK lesions at a Follow-up visit between 12 and 18 months after the Evaluation visit. Subjects received no IRM14 treatment between the Evaluation visit and the Follow-up visit. The 25 cm² treatment area was examined for clinical evidence of AK. The AK recurrence rate for each treatment group was computed as the percentage of complete responders completing the Follow-up visit in each treatment group (77 IRM14-treated, 12 vehicle-treated) that experienced recurrence of AK lesions at the Follow-up visit. The results are summarized in Table 10.

TABLE 10

| Treatment | AK Recurrence Rate |
|---|---|
| IRM14 | 24.7% |
| vehicle | 50.0% |

The complete disclosures of the patents, patent documents and publications cited herein are incorporated by reference in their entirety as if each were individually incorporated. In case of conflict, the present specification, including definitions, shall control.

Various modifications and alterations to this invention will become apparent to those skilled in the art without departing from the scope and spirit of this invention. Illustrative embodiments and examples are provided as examples only and are not intended to limit the scope of the present invention. The scope of the invention is limited only by the claims set forth as follows.

What is claimed is:

1. A method of protecting a subject against UV-induced epidermal neoplasia, the method comprising prophylactic administration to a subject of an immune response modifier (IRM) compound having a 2-aminopyridine fused to a five membered nitrogen-containing heterocyclic ring in an amount effective to provide protection against UV-induced epidermal neoplasia, wherein the IRM compound is administered topically before or during UV exposure to skin not having clinically evident epidermal neoplasia.

2. The method of claim 1 wherein the subject is a mammal.

3. The method of claim 2 wherein the subject is a human.

4. The method of claim 1 wherein the UV-induced epidermal neoplasia is selected from the group consisting of melanoma, basal cell carcinoma, squamous cell carcinoma, actinic keratosis, and pre-actinic keratosis lesions.

5. The method of claim 1 wherein administering the IRM compound protects against epidermal neoplasia induced by UVA or UVB.

6. The method of claim 1 wherein the formulation comprises from about 0.0001% to about 10% IRM compound, by weight.

7. The method of claim 1 wherein the formulation further comprises an adjuvant.

8. The method of claim 1 wherein the topical formulation is a cream, an ointment, an aerosol formulation, a non-aerosol spray, a gel, or a lotion.

9. The method of claim 1 wherein the formulation further comprises at least one sunscreen agent.

10. The method of claim 1 wherein the formulation further comprises a cosmetic.

* * * * *